(12) United States Patent
Kim

(10) Patent No.: US 10,390,799 B2
(45) Date of Patent: Aug. 27, 2019

(54) APPARATUS AND METHOD FOR INTERPOLATING LESION DETECTION

(71) Applicant: Samsung Electronics Co., Ltd., Suwon-si (KR)

(72) Inventor: Ye Hoon Kim, Seoul (KR)

(73) Assignee: Samsung Electronics Co., Ltd., Suwon-si (KR)

(*) Notice: Subject to any disclaimer, the term of this patent is extended or adjusted under 35 U.S.C. 154(b) by 1029 days.

(21) Appl. No.: 14/843,091

(22) Filed: Sep. 2, 2015

(65) Prior Publication Data

US 2016/0058423 A1 Mar. 3, 2016

(30) Foreign Application Priority Data

Sep. 3, 2014 (KR) .................. 10-2014-0117169

(51) Int. Cl.
G06K 9/46 (2006.01)
A61B 8/08 (2006.01)
A61B 6/03 (2006.01)
A61B 8/00 (2006.01)
A61B 6/12 (2006.01)
G06T 7/11 (2017.01)
A61B 5/055 (2006.01)

(52) U.S. Cl.
CPC ............ *A61B 8/5238* (2013.01); *A61B 6/032* (2013.01); *A61B 6/12* (2013.01); *A61B 8/085* (2013.01); *A61B 8/463* (2013.01); *A61B 8/5223* (2013.01); *G06T 7/11* (2017.01); *A61B 5/055* (2013.01); *A61B 2576/00* (2013.01); *G06T 2207/10136* (2013.01); *G06T 2207/20156* (2013.01); *G06T 2207/30096* (2013.01)

(58) Field of Classification Search
None
See application file for complete search history.

(56) References Cited

U.S. PATENT DOCUMENTS

| 8,144,247 B2 | 3/2012 | Kim et al. | |
|---|---|---|---|
| 2008/0037877 A1* | 2/2008 | Jia | G06F 17/30247 382/224 |
| 2009/0034878 A1* | 2/2009 | Sakamoto | G06T 3/4015 382/300 |

(Continued)

OTHER PUBLICATIONS

Bestagini, P. et al, "Detection of temporal interpolation in video sequences," 2013 IEEE International Conference on Acoustics, Speech and Signal Processing (ICASSP), IEEE, 2013 (5 pages).

(Continued)

*Primary Examiner* — Patricia J Park
(74) *Attorney, Agent, or Firm* — Jefferson IP Law, LLP

(57) ABSTRACT

There is provided an apparatus for interpolating a lesion area when diagnosis is performed in a Computer Aided Diagnosis (CAD) system using consecutive images. According to an example, the apparatus includes: an image receiver configured to receive images sequentially; an image matcher configured to match a current image with reference images, and to determine whether to interpolate a lesion area in the current image based on a matching result; and a lesion area acquirer configured to interpolate or acquire the lesion area in the current image according to a result of the determination.

17 Claims, 12 Drawing Sheets

(56) References Cited

U.S. PATENT DOCUMENTS

| | | | | |
|---|---|---|---|---|
| 2009/0190809 A1* | 7/2009 | Han | ............... | G06K 9/48 |
| | | | | 382/128 |
| 2010/0026891 A1* | 2/2010 | Kim | ............... | H04N 7/0127 |
| | | | | 348/459 |
| 2011/0255761 A1* | 10/2011 | O'Dell | ............... | G06T 7/0014 |
| | | | | 382/131 |
| 2013/0322728 A1* | 12/2013 | Jacobs | ............... | A61B 5/055 |
| | | | | 382/132 |
| 2014/0177946 A1* | 6/2014 | Lim | ............... | G06K 9/4614 |
| | | | | 382/156 |
| 2015/0051725 A1* | 2/2015 | Lee | ............... | G09B 23/28 |
| | | | | 700/98 |

OTHER PUBLICATIONS

Jain, R. et al., "Interpolation based tracking for fast object detection in videos," 2011 Third National Conference on Computer Vision, Pattern Recognition, Image Processing and Graphics (NCVPRIPG), IEEE, 2011 (4 pages).

Sadek, R. et al., "Frame Interpolation with Occlusion Detection using a Time Coherent Segmentation," VISAPP, 2012 (6 pages).

Liu, B. et al., "Efficient video duplicate detection via compact curve matching." 2010 IEEE International Conference on Multimedia and Expo (ICME), IEEE, 2010 (6 pages).

\* cited by examiner

APPARATUS AND METHOD FOR INTERPOLATING LESION DETECTION

CROSS-REFERENCE TO RELATED APPLICATION(S)

This application claims the benefit under 35 USC 119(a) of Korean Patent Application No. 10-2014-0117169, filed on Sep. 3, 2014, in the Korean Intellectual Property Office, the entire disclosure of which is incorporated herein by reference for all purposes.

BACKGROUND

1. Field

The following description relates to an apparatus and method for interpolating lesion detection, and more particularly to a technology of interpolating a lesion area when performing diagnosis using consecutive images in a Computer Aided Diagnosis (CAD) system.

2. Description of Related Art

To analyze ultrasonic images acquired in real time from a probe, doctors usually acquire the ultrasonic images by moving the probe in contact with a patient's body, then the doctor detects and determines the presence of a lesion or of a suspected area by looking at the ultrasonic images. If there is a suspected area, the doctor examines the suspected area repeatedly in order to acquire a more accurate and clearer image of the suspected area.

Recently, annalistic techniques using a Computer Aided Diagnosis (CAD) system are commonly used. The CAD system analyzes a medical image to detect a lesion, determines whether the detected lesion is benign or malignant, and provides the doctor with the diagnostic result. However, the analysis is performed by re-examining the suspected area many times.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a detection apparatus including: an image receiver configured to receive images sequentially; an image matcher configured to match a current image with reference images, and to determine whether to interpolate a lesion area in the current image based on a matching result; and a lesion area acquirer configured to acquire a lesion area of the current image by interpolating the lesion area or detect a lesion according to a result of the determination.

The image matcher may be further configured to match the current image with the reference images based on a result of matching two or more previous images with the reference images.

The result of matching the two or more previous images with the reference images may include a current searching direction and index information of the two or more previous images.

The image matcher may be further configured to estimate an index value of the current image based on the result of matching the two or more previous images with the reference images, and to match the current image with a reference image corresponding to the estimated index value among the reference images.

The image matcher may be further configured to extract features from the current image and the reference image corresponding to the estimated index value, and to compare a feature vector of the current image to a feature vector of the reference image corresponding to the estimated index value so as to determine whether the two images match each other.

The image matcher may be further configured to determine that the current image matches the reference image corresponding to the estimated index value among the reference images, in a case where a number of the two or more previous images matching the reference images (is greater than a predetermined threshold.

The lesion area acquirer may be further configured to comprise a lesion area interpolator configured to, in response to a determination to interpolate the lesion area, interpolate the lesion area in the current image using lesion area information of an image that is adjacent to the current image among the reference images.

The lesion area acquirer may be further configured to comprise a lesion area detector configured to, in response to a determination to detect a lesion, detect the lesion from the current image by applying a lesion detection algorithm and set an area where the lesion is detected as a lesion area.

The apparatus may further include a screen display configured to display the acquired lesion area using visually distinguished markers.

In another general aspect, there is provided a detection method including: receiving images sequentially; matching a current image with reference images; based on a matching result, determining whether to interpolate a lesion area in the current image; and acquiring the lesion area of the current image by interpolating the lesion area or by detecting a lesion according to a result of the determination.

The matching of the current image with the reference images may include matching the current image with the reference images based on a result of matching two or more previous images (with the reference images.

The result of matching the two or more previous images with the reference images may include a current searching direction and index information of the two or more previous images.

The matching of the current image with the reference images based on the result of matching the two or more previous images with the reference images may include: estimating an index value of the current image using the result of matching the two or more previous images with the reference images; and matching the current image with a reference image corresponding to the estimated index value among the reference images.

The matching of the current image with the reference image corresponding to the estimated index value may include: extracting features from the current image and the reference image corresponding to the estimated index value; and comparing a feature vector of the current image with a feature vector of the reference image corresponding to the estimated index value so as to determine whether the two images match each other.

The matching of the current image with the reference image corresponding to the estimated index value may include: determining whether a number of the two or more previous images matching the reference images is greater than a predetermined threshold; and, in response to a determination that the number of the two or more previous images matching the reference images is greater than the predetermined threshold, determining that the current image matches the reference image corresponding to the estimated index value.

The acquiring of the lesion area may include, in response to a determination to interpolate the lesion area, interpolating the lesion area in the current image using lesion area information of an images is adjacent to the current image among the reference images.

The acquiring of the lesion area may include: in response to a determination to detect the lesion, detecting the lesion from the current image by applying a lesion detection algorithm; and setting an area where the lesion is detected as the lesion area The method may further include displaying the acquired lesion area using a visually distinguished marker.

In another general aspect, there is provided a detection method including receiving images, and matching a currently received image with each of cross-sectional images of a pre-constructed three-dimensional (3D) model, in response to the currently received image matching any one of the cross-sectional images of the pre-constructed 3D model determining that the currently received image is being re-examined and acquiring lesion area information of the matching cross-sectional images of the pre-construed 3D model as a lesion area of the currently received image, and in response to the currently received image not matching any of the cross-sectional images of the pre-constructed 3D model detecting the lesion area from the currently received image.

Other features and aspects may be apparent from the following detailed description, the drawings, and the claims.

Figure 1:
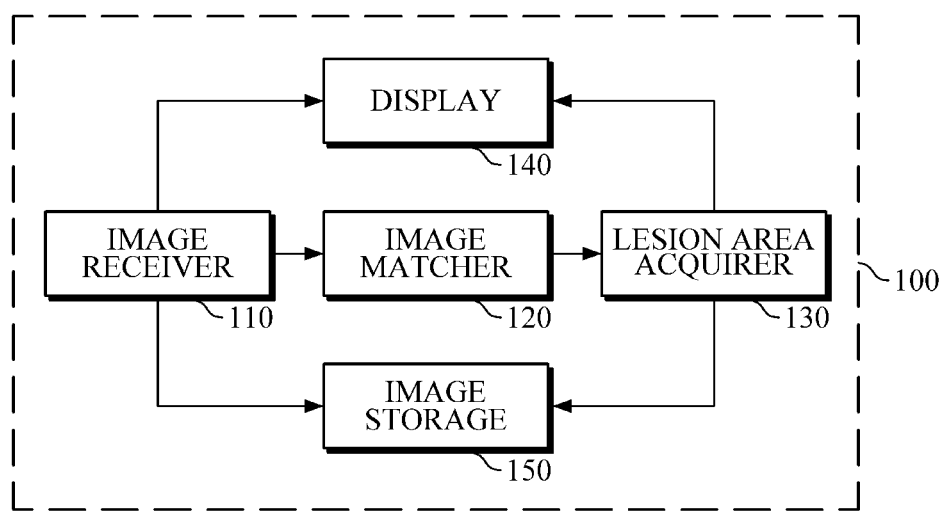
FIG. 1 is a block diagram illustrating an example of an apparatus for interpolating lesion detection.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. For example, the sequences of operations described herein are merely examples, and are not limited to those set forth herein, but may be changed as will be apparent to one of ordinary skill in the art, with the exception of operations necessarily occurring in a certain order. Also, descriptions of well-known functions and constructions may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Hereinafter, an apparatus and method for interpolating lesion detection are described in detail with reference to drawings.

Figure 2:
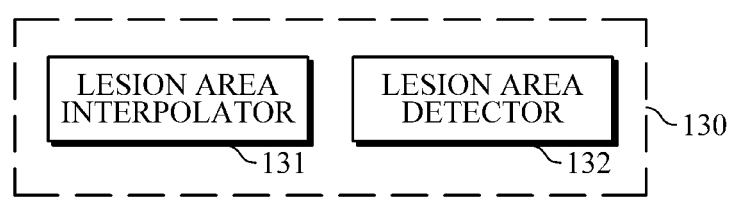
FIG. 2 is a block diagram illustrating an example of a lesion area acquirer shown in the example of FIG. 1.

FIG. 1 is a block diagram illustrating example of an apparatus for interpolating lesion detection. FIG. 2 is a block diagram illustrating an example of a lesion area acquirer shown in the example of FIG. 1.

Referring to FIG. 1, an apparatus 100 for interpolating lesion detection includes an image receiver 110, an image matcher 120, a lesion area acquirer 130, a display 140, and an image storage 150. Although FIG. 1, illustrates the image receiver 110, the image matcher 120, the lesion area acquirer 130, the display 140, and the image storage 150 included in the apparatus 100, these components may be embodied as independent hardware. Therefore, the apparatus 100 illustrated in FIG. 1 is not limited thereto and thus may include more or less components.

The image receiver 110 receives medical images from an image acquiring device. A medical image may be an ultrasonic image of an examined area, which is captured by a probe in real time. The medical images may be consecutive images received in real time in units of frames. In addition, the medical images may be of images sequentially received to form an image sequence. However, aspects of the present application are not limited thereto, and a medical image may include a Computed Radiography (CR) scan, a Computed Tomography (CT) scan, a Magnetic Resonance Image (MRI), and any other medical image.

When a current image is received, the image matcher 120 matches the current image with reference images. The reference images may be previously acquired two-dimensional (2D) images in sequence of an examined area.

The image matcher 120 may determine whether the current image matches any reference image, by comparing the current image with all the reference images. The image matcher 120 may determine whether the current image matches any reference image, by comparing the current image with all the reference images on the basis of pixel or preset pixel group unit. For example, the image matcher 120 may extract features from all the pixels of the current image and each of the reference images by using a feature extraction algorithm, and may determine whether the current image matches any reference image by comparing feature vectors between the current image and each of the reference images. The feature extraction algorithm may include a Scale Invariant Feature Transform (SIFT), Speeded Up Robust Features (SURF), and Binary Robust Invariant Scalable Keypoints (BRISK), According to another embodiment, instead of comparing the current image with all the reference images, the image matcher 120 may estimate an index value of the current image using a result of matching two or more previous images with the reference image, and determine whether the current image matches a reference image corresponding to the estimated index value. The matching result of the previous images may include index information of each previous image and searching orientation information.

For example, the image matcher 120 may determine whether the current image matches a reference image corresponding to the estimated index value thereof by comparing the current image and each of the reference images on the basis of pixel or pixel group unit, as described above. In another example, in a case where the number of previous images matching the reference images is greater than a predetermined threshold, the image matcher 120 may determine that the current image matches a reference image corresponding to the estimated index value without comparing the current image with the reference image.

According to yet another embodiment, in a case where the same examined area is re-examined using a probe localization technique, the image matcher 120 may determine whether the current image matches a reference image by using location information of the current image and the reference image. For example, by estimating the current location of a probe using an accelerometer/camera module equipped in the probe or a camera installed on a ceiling of an examination site, the image matcher 120 may determine whether the same examined area as that of the matching reference image is re-examined.

According to a result of matching the current image with the reference image, the image matcher 120 determines whether to interpolate a lesion area in the current image.

For example, in a case where there is a reference image matching the current image, the image matcher 120 may determine to interpolate a lesion area in the current image. Alternatively, in a case where there are no reference images matching the current image, that is, the current image is a new image, the image matcher 120 may determine to detect a lesion area from the current image.

In another example, even in a case where there is a reference image matching the current image, if an image to be used for interpolating a lesion area, that is, a left image (captured at a previous time) or a right image (captured at a subsequent time) of the matching reference image does not have lesion area information items greater than a preset numeric value, the image matcher 120 may determine to detect a new lesion area from the current image. However, the above is merely exemplary, and various standards for determination as to whether to interpolate a lesion area may be determined.

The lesion area acquirer 130 acquires a lesion area from the current image. The image acquirer 130 may acquire a lesion area by interpolating or detecting the lesion area with respect to the current image according to a determination made by the image matcher 120.

Referring to FIG. 2, the lesion area acquirer 130 includes a lesion area interpolator 131 and a lesion area detector 132. Although FIG. 2 illustrates the lesion area interpolator 131 and a lesion area detector 132 included in the lesion area acquirer 130, these components may be embodied as independent hardware. Therefore, the lesion area acquirer 130 illustrated in FIG. 2 is not limited thereto and thus the lesion area acquirer 130 may include more or less components.

In response to a determination made to interpolate a lesion area in the current image, the lesion area interpolator 131 may interpolate a lesion area using lesion area information of a left/right image of a reference image matching the current image. In this case, if the matching reference image already has lesion area information, the lesion area interpolator 131 may directly acquire a lesion area from the current image using information on the lesion area (e.g., location and size), without interpolating the lesion area.

According to a preset standard, the lesion area interpolator 131 may interpolate the lesion area by taking into account either or both of a left image and a right image, which are close to the current image. In addition, the lesion area interpolator 131 may interpolate the lesion area using two or more preset left/right images.

In response to a determination made to detect a lesion area from the current image, the lesion area detector 132 may detect a lesion, by applying a lesion detection algorithm to the current image, and set an area including the detected lesion as a lesion area. The lesion detection algorithm may include AdaBoost, deformable Part Models (DPM), Deep Neural Network (DNN), Convolutional Neural Network (CNN), Sparse Coding, and the like. However, aspects of the present application are not limited thereto.

The display 140 may output a current image on a screen. In addition, when the lesion area acquirer 130 acquires a lesion area from the current image output on the screen, the display 140 may show the lesion area by displaying, at a corresponding location, visual information such as a bounding box, a circle, an oval, a cross, and the like. The display 140 may display the visual information of various colors, line types, and line thickness so as to enable a doctor to identify the lesion area.

The image storage 150 may store a reference image that is previously acquired with respect to an examined area. In addition, when the image receiver 110 receives an image, the image storage 150 may store the current image as a reference image to be used when matching a subsequent image to be received.

Figure 3A:
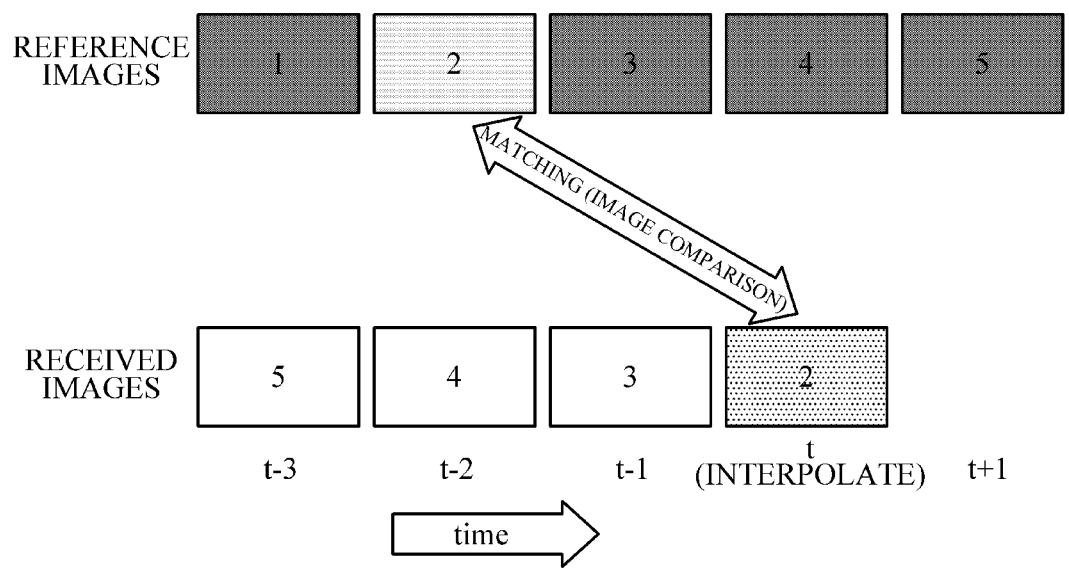
FIGS. 3A and 3B are examples for explaining how to match a current image with a reference image.
Figure 3B:
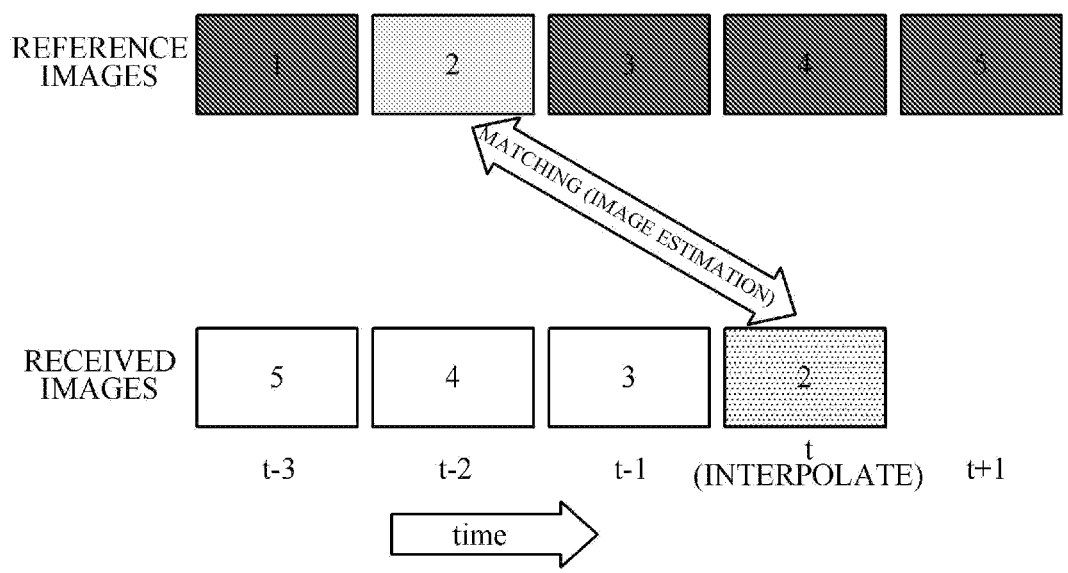

FIGS. 3A and 3B are examples for explaining how to match a current image with a reference image. The examples of FIGS. 3A to 3B are described using the apparatus shown in FIG. 1.

Five pre-stored reference images are illustrated in an upper part of each of FIGS. 3A and 3B and images that are received sequentially are illustrated in a bottom part of FIGS. 3A and 3B. The reference images are image sequences with index values of 1, 2, 3, 4, and 5. The image sequences with index values of 1, 3, 4, and 5 include lesion area information, but the image sequence with an index value of 2 does not include lesion area information Referring to FIG. 3A, when an image at a current time (t) is received, the image matcher 120 compares the image at the current time (t) with reference image 2. At this point, as described above, the image matcher may estimate an index value of the image at the current time (t) using matching results of the two or more images at previous times (t-3), (t-2) and (t-1), for example, index information and searching direction information of each previous image. As shown in FIG. 3A, index for the images received at (t-3), (t-2), and (t-1) are 5, 4, and 3, respectively, indicating that a search is being performed in a backward direction. Based on the above, it is possible to estimate that an index value of the image at the current time (t) is 2.

When an index value of the image at the current time (t) is estimated, the image matcher 120 may compare in detail the reference 2 with an index value of 2 with the image at the current time (t) so as to determine whether the reference image 2 matches the image at the current time (t). If it is found that the reference image 2 matches the image at the current time (t), the image matcher 120 may determine to interpolate a lesion area in the image at the current time (t), and, if not, the image matcher 120 may determine to detect a lesion area from the image at the current time (t).

Similar to FIG. 3A, FIG. 3B is a diagram illustrating an example in which an image matcher 120 matches the image at the current time (t) with reference images using matching results of previous images at previous times (t-3), (t-2) and (t-1). As shown in FIG. 3B, three images at previous times (t-3), (t-2), and (t-1) match reference images 5, 4, and 3, respectively, indicating a backward search direction. Thus, the image matcher 120 may estimate that an index value of the image at the current time (t) is 2. If a threshold predetermined for the current time (t) is set to 3 and thereby three images at previous times (t-3), (t-2), and (t-1) match the reference images, the image matcher 120 may determine that the image at the current time (t) matches a reference image with an index value of 2 without performing a detailed comparison, and thus, the image matcher 120 may determine to interpolate a lesion area.

Figure 4A:
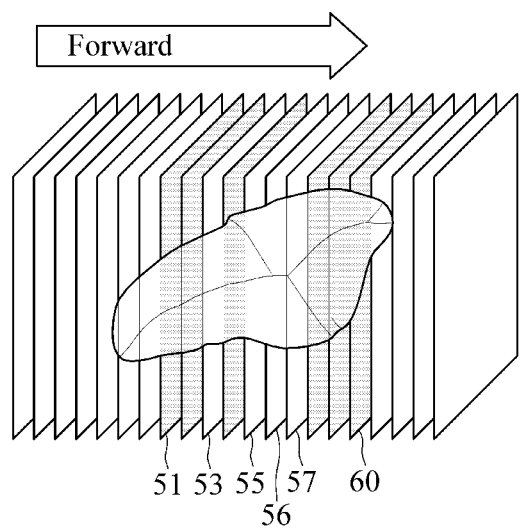
FIGS. 4A, 4B and 4C are examples for explaining of how to interpolate a lesion area in the current image.

FIGS. 4A. 4B and 4C are examples for explaining how to interpolate a lesion area in the current image.

Figure 4B:
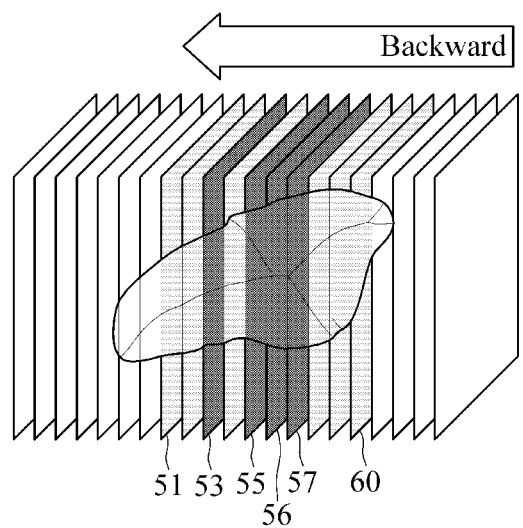

FIG. 4A illustrates reference image data that is consecutively acquired by searching an examined area in a forward direction. FIG. 4A shows a lesion first detected from a reference image 51 and last detected from a reference image 60, but not detected from some of the images between the two images 51 and 60. FIG. 4B illustrates a process of searching the same examination area in a backward direction. The reference images 57, 56, 55, and 53, which match the received images 57, 56, 55, and 53, respectively, do not include lesion area information, and thus, a lesion area is acquired from the received images 57, 56, 55, and 53 by interpolating the lesion area, as shown in FIG. 4C.

Figure 4C:
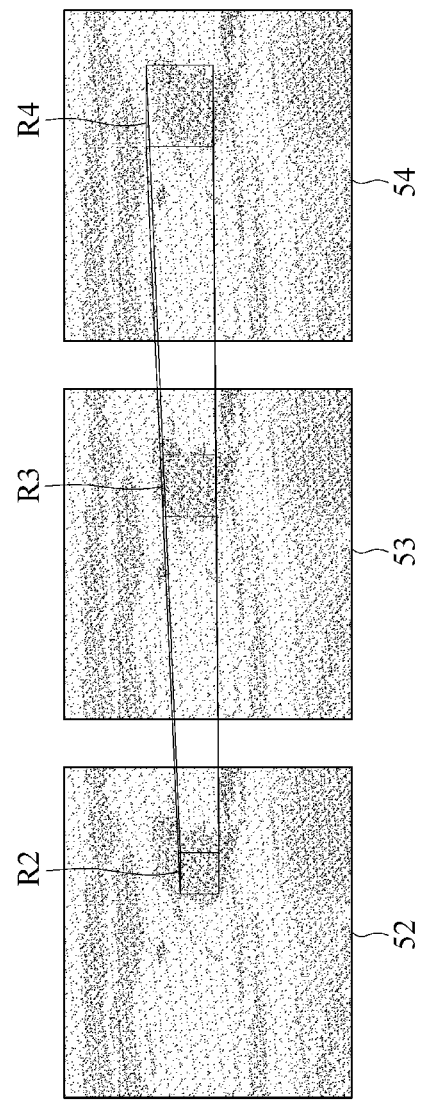

FIG. 4C illustrates the lesion area acquirer 130 interpolating a lesion area R3 using lesion area information (e.g., size and location of a lesion area) of lesion areas R2 and R4 in images 52 and 54 on the left-hand side and the right-hand side of a reference image that matches the current image 53. By doing so, it is not necessary to re-acquire a lesion area using a lesion detection algorithm, thereby minimizing a time for acquiring a lesion area.

Although FIG. 4C illustrates an example explaining how to interpolate a lesion area in the current image 53, the method is not limited thereto and thus the same method may be applied when interpolating a lesion area in the current images 57, 56, and 55. In a case when lesion area information does not exist in a left/right image of a current image, a determination may be made to detect a new lesion area, without interpolating a lesion area. For example, none of images 55, 56 and 57 include lesion area information.

Figure 5:
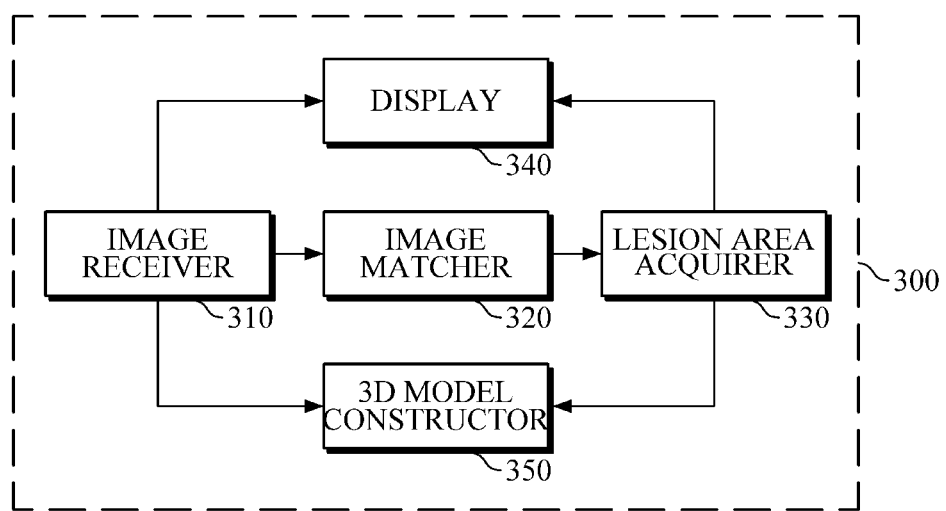
FIG. 5 is a block diagram illustrating another example of an apparatus for interpolating lesion detection.
Figure 6:
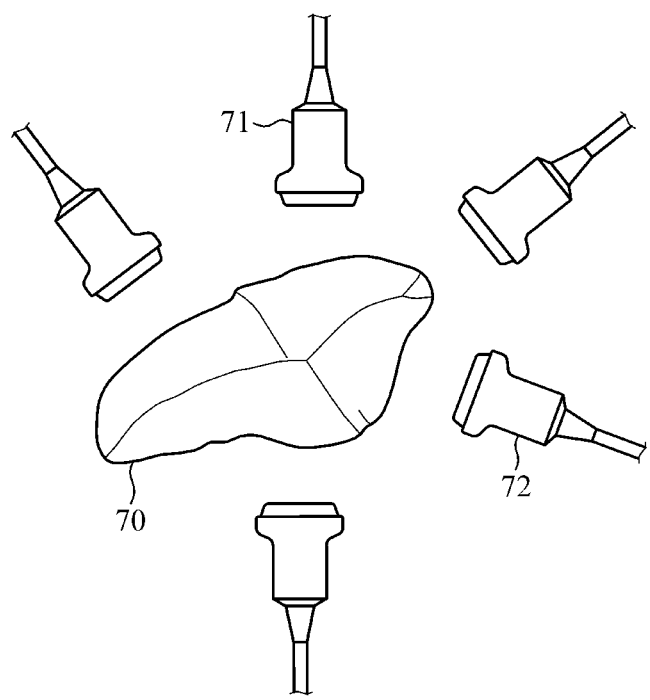
FIG. 6 is a diagram for explaining how to match a current image with a three-dimensional (3D) model.

FIG. 5 is a block diagram illustrating another example of an apparatus for interpolating lesion detection. FIG. 6 is a diagram for explaining how to match a current image with a three-dimensional (3D) model.

Referring to FIG. 5, an apparatus 300 for interpolating lesion detection includes an image receiver 310, an image matcher 320, a lesion area acquirer 330, a display 340, and a 3D model constructor 350.

Referring to FIG. 6, a doctor may place a probe in contact with an examined area 70 at various angles in various directions and acquire images of the examined area 70. In a case where a doctor acquires the first 2D cross-sectional image by moving a probe 71 in contact with the examined area 70 in a first direction, which enables matching reference images, it is possible to acquire a lesion area by interpolating the lesion area by matching a first image with reference images, as described above. Then, if the doctor acquires the second image by moving the probe 72 in contact with the examined area 70 in a second direction different from the first direction, it is difficult to acquire a lesion area by matching a second image with the reference images. According to an exemplary embodiment, even when acquiring images of the same examined area 70 by using a probe at various positions and angles, it is possible to easily acquire a lesion area.

Again, referring to FIG. 5, the image receiver 310 receives images of an examined area. When the first image of an examined area is received, the image matcher 320 matches the first image with reference images so as to determine whether to interpolate a lesion area, and the lesion area acquirer 330 acquires a lesion area by interpolating or detecting the lesion area in the first image. The display 340 may visually display the lesion area on a screen using a bounding box, a circle, an oval, a cross, and the like.

The 3D model constructor 350 constructs a 3D model of the examined area using the first image and acquired lesion area information.

Then, if a doctor acquires the second image of the same examined area from the second direction, which is hard to match with the reference images, the image matcher 310 receives the second image.

In response to the receipt of the second image, the image matcher 320 compares the second image with each cross-sectional image of a 3D model previously constructed by the model constructor 350, and determines whether the same examined area is being re-examined.

If it is determined that the same area is re-examined, the lesion area acquirer 330 acquires a lesion area from the second image as lesion area information of a cross sectional image that matches the second image among all the cross-sectional images of the pre-constructed 3D model.

The display 340 visually displays the lesion area of the second image using the acquired lesion area information.

Figure 7:
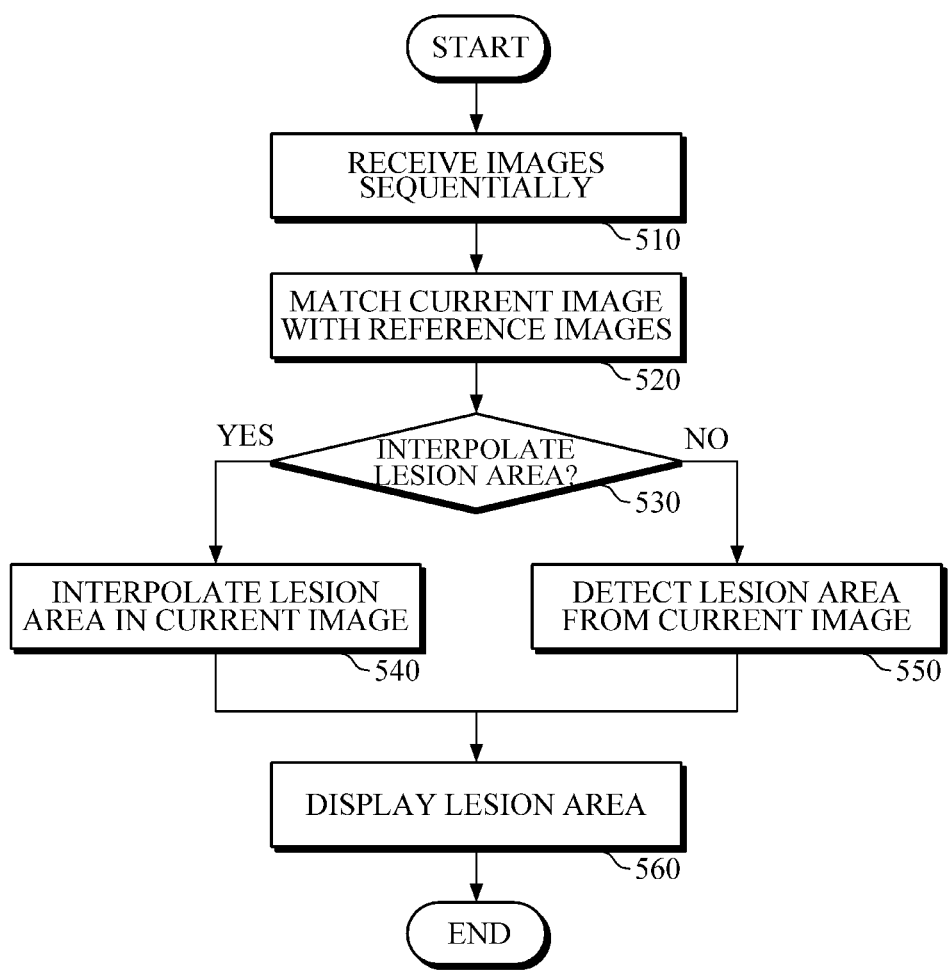
FIG. 7 is a flowchart illustrating an example of a method for interpolating lesion detection.
Figure 8:
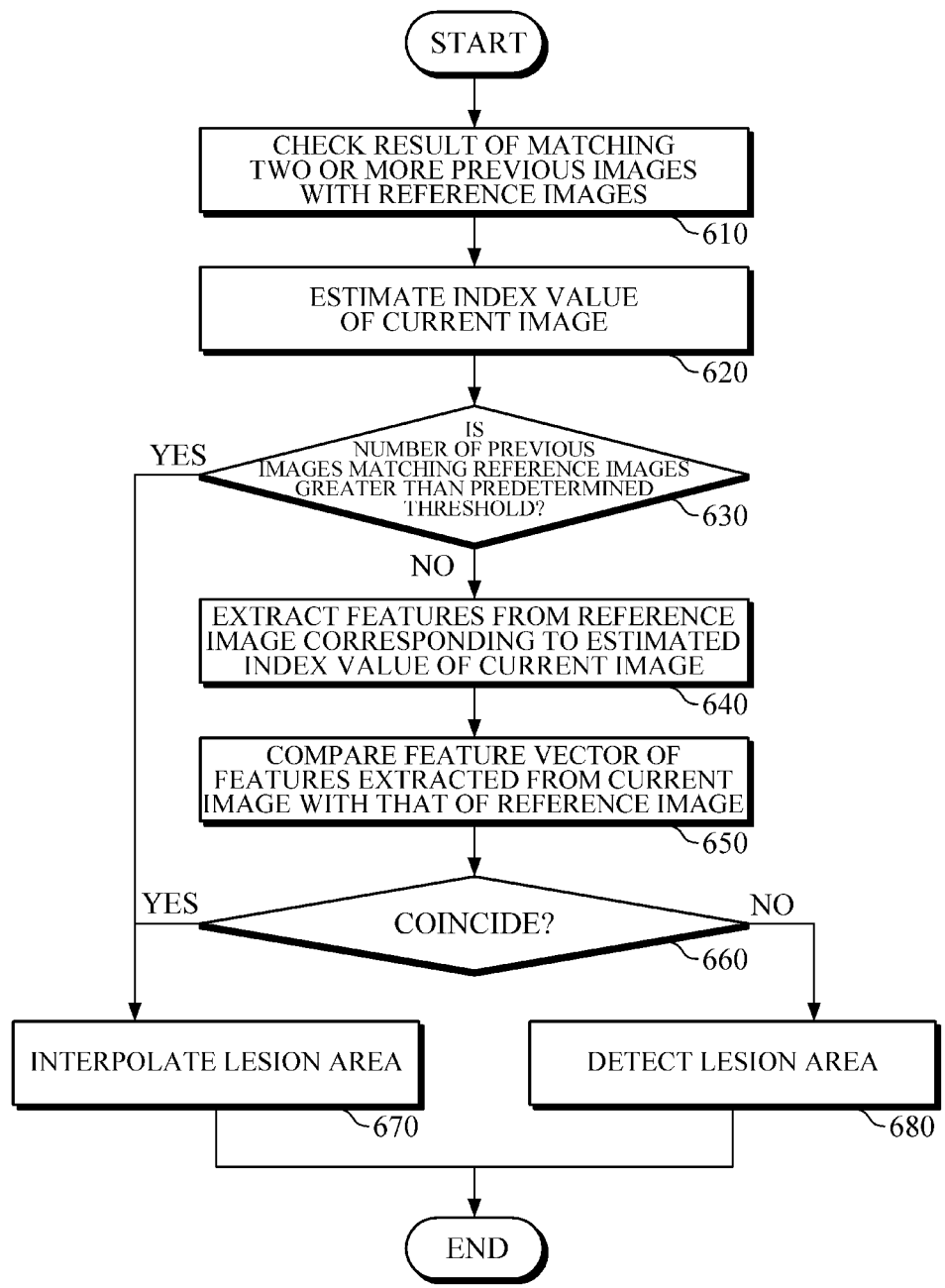
FIG. 8 is a flowchart illustrating in detail operations shown in FIG. 7.

FIG. 7 is a flowchart illustrating an example of a method for interpolating lesion detection. FIG. 8 is a flowchart illustrating operations shown in FIG. 7.

FIGS. 7 and 8 are examples of a method for interpolating lesion detection, which is implemented by the apparatus shown in the example of FIG. 1.

The apparatus 100 may sequentially receive medical images from an image acquiring device in operation 510. A medical image may be an ultrasonic image, a CR scan, a CT scan, an MRI, and any other medical image. The medical images may be received in real time in units of frames and may be consecutive images that form a sequence.

Then, the apparatus 100 matches a current image with reference images in operation 520, and the apparatus 100 determines whether to interpolate a lesion area according to the matching result in operation 530.

Hereinafter, operations 520 and 530 are described in detail with reference to FIG. 8.

Referring to FIG. 8, the apparatus 100 checks a result of matching two or more previous images with the reference images in operation 610. At this time, the matching result may be generated by comparing the previous images with the reference images on the basis of pixel or pixel group unit, and the matching result may include index information of the previous images and the current search-direction information.

Then, the apparatus 100 estimates an index value of the current image using the matching result of the previous images in operation 620. As illustrated in FIGS. 3A and 3B, three previous images have index values of 5, 4, and 2, indicating a backward search direction. As a result, the apparatus 100 may estimate that an index value of the current image is 2.

Then, the apparatus 100 may determine whether the number of previous images matching the reference images is greater than a predetermined threshold in operation 630. In response to a determination made in operation 630 that the number of previous images matching the reference images is greater than the predetermined threshold, the apparatus 100 may determine in operation 670 to interpolate a lesion area in the current image without comparing the current image with a reference image corresponding to an estimated index value thereof.

Alternatively, in response to a determination made in operation 630 that the number of previous images matching the reference images is less than the predetermined threshold, the apparatus 100 extracts features from the current image and a reference image corresponding to an estimated index value thereof in operation 640, and compares a feature vector of the features extracted from the current image with that of the reference image in operation 650.

If it is found in operation 660 that the feature vector of the current image coincides with that of the reference image, the apparatus 100 interpolates a lesion area in the current image in operation 670. If it is not found in operation 660 that the feature vector of the current image coincides with that of the reference image, the apparatus 100 determines to detect a lesion area from the current image in operation 680.

Again, referring to FIG. 7, in response to a determination made in operation 530 to interpolate a lesion area in the current image, the apparatus 100 may determine to interpolate a lesion area in the current image using lesion area information (e.g., location, size, and the like) of images on the left-hand side/right-hand side of the current image among all reference images, without detecting a lesion from the current image in operation 540. Alternatively, in response to a determination made in operation 530 not to interpolate a lesion area in the current image, the apparatus 100 may detect a lesion area from the current image in operation 550 by applying a lesion detection algorithm to the current image. The lesion detection algorithm may include AdaBoost, deformable Part Models (DPM), Deep Neural Network (DNN), Convolutional Neural Network (CNN), Sparse Coding, and the like.

Then, a lesion area is acquired by performing interpolation or detection with respect to the current image, the apparatus 100 may display the acquired lesion area on a screen using various visual methods in operation 560.

Figure 9:
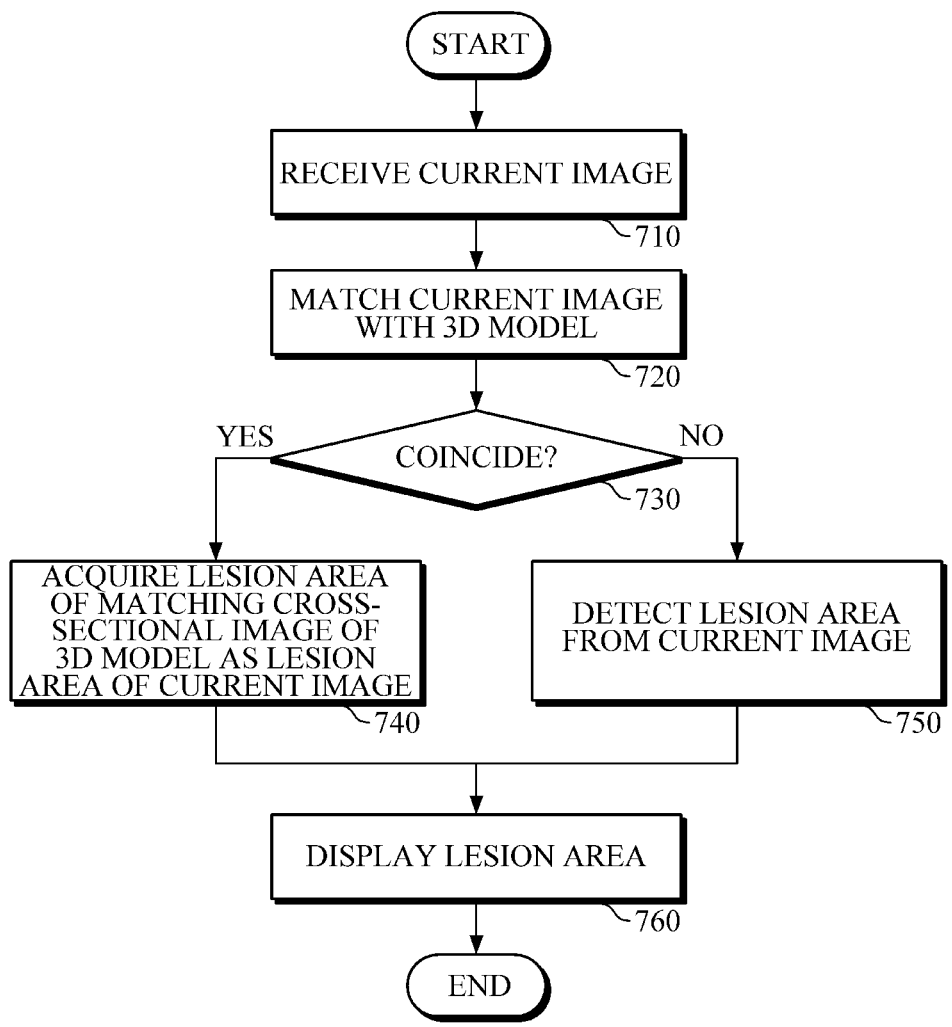
FIG. 9 is a flowchart illustrating an example of a method for interpolating lesion detection.

FIG. 9 is a flowchart illustrating an example of a method for interpolating lesion detection.

FIG. 9 is an example of a method for interpolating lesion detection, which is implemented by the apparatus as shown in the example of FIG. 5.

When a current image is received in operation 710, the apparatus 300 matches the current image with each cross-sectional image of a pre-constructed 3D model in operation 720.

In a case where the current image matches any cross-sectional image of the 3D model in operation 730, the apparatus 300 determines that the same examined area is being re-examined, and then acquires lesion area information of the matching cross-sectional image of the 3D model as a lesion area of the current image in operation 740. In a case where the current image does not match any cross-sectional image of the 3D model, the apparatus 300 determines that a different area is examined, and detects a lesion area from the current image in operation 750 by applying a lesion detection algorithm to the current image.

Then, the apparatus 300 displays information on the lesion area acquired from the current image using various visual elements in operation 760.

The application can also be embodied as computer readable codes found on a non-transitory computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, and carrier waves (such as data transmission through the Internet). The non-transitory computer readable recording medium can also be distributed over network coupled computer systems so that the computer readable code is stored and executed in a distributed fashion. Also, functional programs, codes, and code segments for accomplishing the present application can be easily construed by programmers skilled in the art to which the present application pertains.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A detection apparatus comprising:
a memory configured to store instructions; and
at least one processor, when executing the stored instructions, is configured to:
receive a sequence of first images inputted in real time,
match a current image of the sequence of first images with a second image of reference images, the reference images previously stored prior to the receiving of the sequence of first images,
determine whether to interpolate a lesion area in the current image based on a matching result,
in response to determining that the current image is matched with the second image, acquire the lesion area of the current image by interpolating, based on the second image, the lesion area, and
in response to determining that the current image is not matched with the second image, detect the lesion area of the current image by using a lesion area detection algorithm.

2. The apparatus of claim 1, wherein the at least one processor is further configured to match the current image with the second image of the reference images based on a result of matching two or more previous images of the sequence of first images with the reference images.

3. The apparatus of claim 2, wherein the result of matching the two or more previous images with the reference images comprises a current searching direction and index information of the two or more previous images.

4. The apparatus of claim 2, wherein the at least one processor is further configured to:
estimate an index value of the current image based on the result of matching the two or more previous images with the reference images, and match the current image with the second image corresponding to the estimated index value among the reference images.

5. The apparatus of claim 4, wherein the at least one processor is further configured to:
extract features from the current image and the second image corresponding to the estimated index value, and
compare a feature vector of the current image to a feature vector of the second image corresponding to the estimated index value so as to determine whether the current image and the second image match each other.

6. The apparatus of claim 4, wherein the at least one processor is further configured to determine that the current image matches the second image corresponding to the estimated index value among the reference images, when a number of the two or more previous images matching the reference images is greater than a predetermined threshold.

7. The apparatus of claim 1, wherein the at least one processor is further configured to, in response to a determination to interpolate the lesion area, interpolate the lesion area in the current image using lesion area information of an image that is adjacent to the second image among the reference images.

8. The apparatus of claim 1, further comprising:
a screen display configured to display the acquired lesion area using visually distinguished markers.

9. A detection method of an apparatus comprising:
receiving, by at least one processor of the apparatus, a sequence of first images inputted in real time;
matching, by at least one processor, a current image of the sequence of first images with a second image of reference images, the reference images previously stored in a memory of the apparatus prior to the receiving of the sequence of first images;
determining whether to interpolate a lesion area in the current image based on a matching result;
in response to determining that the current image is matched with the second image, acquiring the lesion area of the current image by interpolating, based on the second image, the lesion area; and
in response to determining that the current image is not matched with the second image, detecting the lesion area of the current image by using a lesion area detection algorithm.

10. The method of claim 9, wherein the matching of the current image with the second image of the reference images comprises matching the current image with the second image of the reference images, based on a result of matching two or more previous images of the sequence of first images with the reference images.

11. The method of claim 10, wherein the result of matching the two or more previous images with the reference images comprises a current searching direction and index information of the two or more previous images.

12. The method of claim 10, wherein the matching of the current image with the second image of the reference images based on the result of matching the two or more previous images with the reference images comprises:
estimating an index value of the current image using the result of matching the two or more previous images with the reference images; and
matching the current image with the second image corresponding to the estimated index value among the reference images.

13. The method of claim 12, wherein the matching of the current image with the second image corresponding to the estimated index value comprises:
extracting features from the current image and the second image corresponding to the estimated index value; and
comparing a feature vector of the current image with a feature vector of the second image corresponding to the estimated index value so as to determine whether the current image and the second image match each other.

14. The method of claim 12, wherein the matching of the current image with the second image corresponding to the estimated index value comprises:
determining whether a number of the two or more previous images matching the reference images is greater than a predetermined threshold; and
in response to a determination that the number of the two or more previous images matching the reference images is greater than the predetermined threshold, determining that the current image matches the second image corresponding to the estimated index value.

15. The method of claim 9, wherein the acquiring of the lesion area comprises, in response to a determination to interpolate the lesion area, interpolating the lesion area in the current image using lesion area information of an image that is adjacent to the second image among the reference images.

16. The method of claim 9, further comprising: displaying the acquired lesion area using a visually distinguished marker.

17. The method of claim 9, wherein the sequence of first images the images are received sequentially.

* * * * *